(12) United States Patent
Seward

(10) Patent No.: US 9,361,430 B2
(45) Date of Patent: Jun. 7, 2016

(54) DETERMINING DISEASE STATE OF A PATIENT BY MAPPING A TOPOLOGICAL MODULE REPRESENTING THE DISEASE, AND USING A WEIGHTED AVERAGE OF NODE DATA

(71) Applicant: RENEW GROUP PRIVATE LIMITED, Singapore (SG)

(72) Inventor: James B. Seward, Rochester, MN (US)

(73) Assignee: Renew Group Pte. Ltd., Singapore (SG)

(*) Notice: Subject to any disclaimer, the term of this patent is extended or adjusted under 35 U.S.C. 154(b) by 0 days.

(21) Appl. No.: 14/853,355

(22) Filed: Sep. 14, 2015

(65) Prior Publication Data
US 2016/0004830 A1 Jan. 7, 2016

Related U.S. Application Data

(63) Continuation-in-part of application No. 14/278,648, filed on May 15, 2014, now Pat. No. 9,135,399, which is a continuation-in-part of application No. 13/903,496, filed on May 28, 2013.

(60) Provisional application No. 61/651,797, filed on May 25, 2012.

(51) Int. Cl.
*G06F 19/00* (2011.01)
*G06N 5/02* (2006.01)

(52) U.S. Cl.
CPC .......... *G06F 19/345* (2013.01); *G06F 19/3431* (2013.01); *G06N 5/022* (2013.01); *G01N 2800/00* (2013.01)

(58) Field of Classification Search
CPC ............ G06F 19/3431; G06F 19/3437; G01N 2800/00
USPC .................................................. 706/12, 45, 62
See application file for complete search history.

(56) References Cited

U.S. PATENT DOCUMENTS

| | | | |
|---|---|---|---|
| 2008/0195643 A1 | 8/2008 | Sheth-Voss et al. | |
| 2008/0306914 A1* | 12/2008 | Jensen | G06F 17/30722 |
| 2009/0024615 A1 | 1/2009 | Pedro et al. | |
| 2009/0083203 A1 | 3/2009 | Cho et al. | |
| 2009/0157663 A1 | 6/2009 | Kate | |
| 2010/0217094 A1* | 8/2010 | Seward | G06F 19/3443 600/300 |
| 2012/0035855 A1* | 2/2012 | Li | G06F 19/12 702/19 |
| 2012/0296569 A1* | 11/2012 | Shahaf | A61B 5/048 702/19 |
| 2013/0317320 A1* | 11/2013 | Seward | G06F 19/345 600/301 |
| 2014/0222738 A1* | 8/2014 | Joyce | G06N 3/10 706/13 |
| 2014/0249841 A1* | 9/2014 | Seward | G06F 19/3431 705/2 |

OTHER PUBLICATIONS

D.W. Aha et al., "Instance-Based Learning Algorithms," Machine Learning, 1991, vol. 6, p. 37-66.

(Continued)

*Primary Examiner* — David Vincent
(74) *Attorney, Agent, or Firm* — Oakland Law Group PLLC

(57) ABSTRACT

A medical general intelligence computer system and computer-implemented methods analyze morpho-physiological numbers for determining a risk of an emergent disease state, determining an emergent disease state, predicting a pre-emergent disease state, determining a pre-emergent disease state, and/or predicting a risk of a pre-emergent disease state.

6 Claims, 11 Drawing Sheets

(56) References Cited

OTHER PUBLICATIONS

"Artificial Intelligence in Medicine (AIM)," found online at https://www.cedars-sinai.edu/Patients/Programs-and-Services/Medicine-Department/Artificial-Intelligence-in-Medicine-AIM/ on Dec. 7, 2013 (2 pages).

A-L Barabási, excerpt of "Linked: How Everything is Connected to Everything Else and What It Means for Business, Science, and Everyday Life," published by Plume, 2003, p. 65-78.

A.X. Garg et al., "Effects of Computerized Clinical Decision Support Systems on Practitioner Performance and Patient Outcomes: A Systematic Review," JAMA, 2005, vol. 293, No. 10, p. 1223-1238.

N.L. Griffin and F.D. Lewis, "A Rule-Based Inference Engine which is Optimal and VLSI Implementable," found online at http://www.cs.uky.edu/~lewis/papers/inf-engine.pdf, available at least by Dec. 19, 2013, 14 pages.

J.P. Kassirer, "Diagnostic Reasoning," Annals of Internal Medicine, 1989, vol. 110, No. 11, p. 893-900.

A.J. Lusis and J.N. Weiss, "Cardiovascular Networks: Systems-Based Approaches to Cardiovascular Disease," Circulation, 2010, vol. 121, p. 157-170.

P. Wang, "A New Approach for Induction: From a Non-Axiomatic Logical Point of View," Center for Research on Concepts and Cognition, Indiana University, 1995, 18 pages.

* cited by examiner

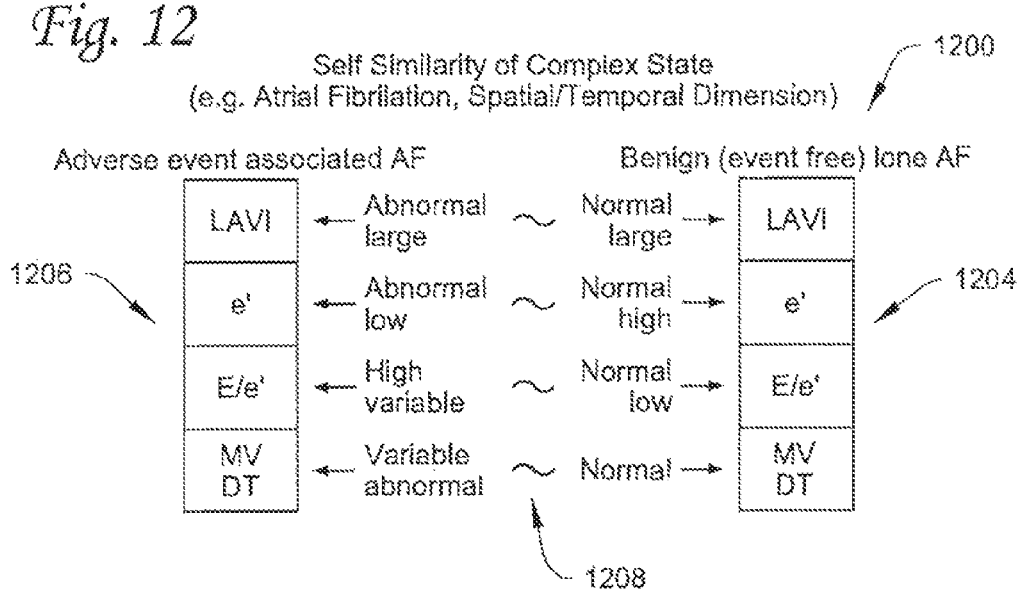

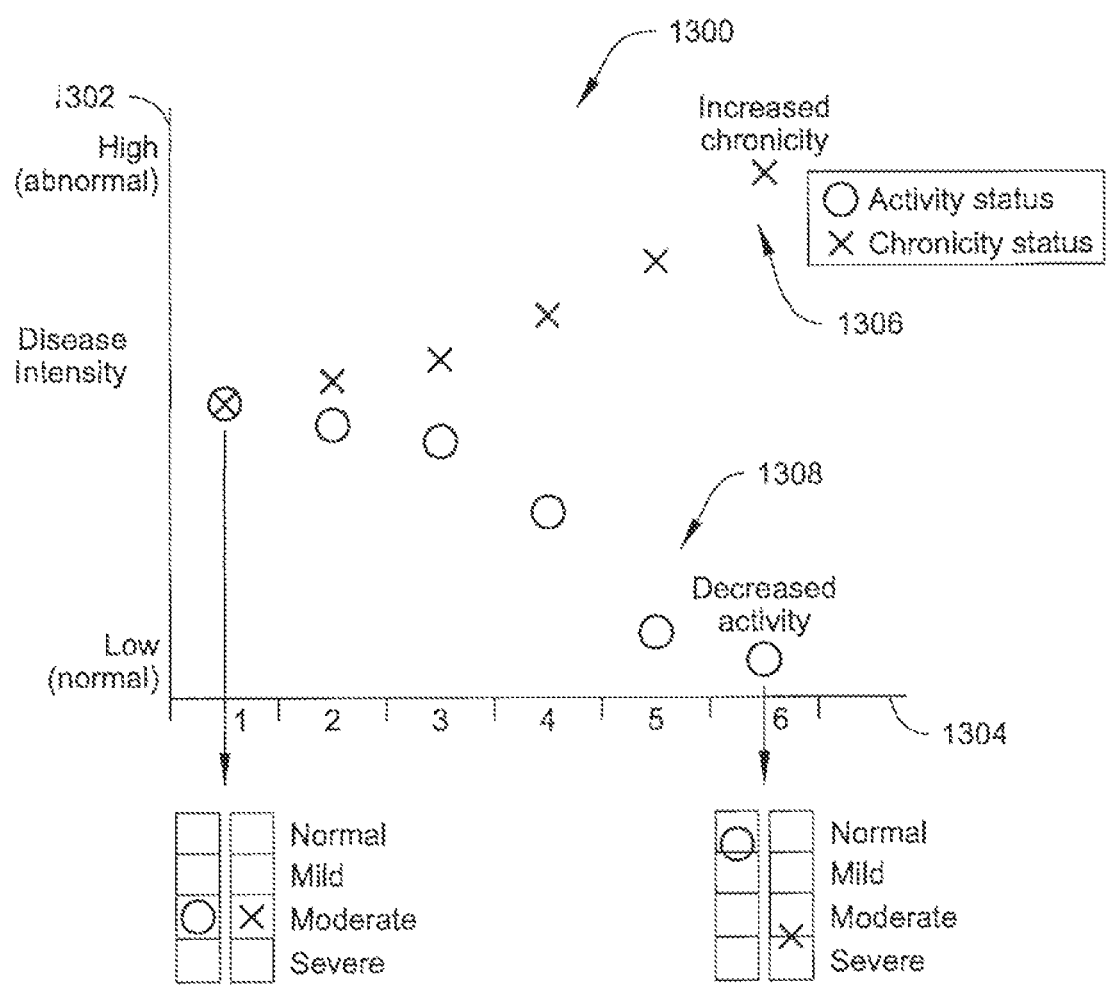

US 9,361,430 B2

DETERMINING DISEASE STATE OF A PATIENT BY MAPPING A TOPOLOGICAL MODULE REPRESENTING THE DISEASE, AND USING A WEIGHTED AVERAGE OF NODE DATA

FIELD

This disclosure generally relates to an artificial intelligence system applied to the medical arts and a computerized method for making a medical diagnosis.

BACKGROUND

Biological systems are complex. Complex means that the data is nonlinear and/or dynamic. Generally, determining a risk of an emergence of a disease state (e.g., emergent disease state; a phenotype of a disease state being expressed) is an unsolvable problem in polynomial time, exponential time, or finite time. Further, generally, predicting a pre-emergence of a disease state (e.g., pre-emergent disease state; prior to actual emergence of that disease state) is an unsolvable problem in polynomial time, exponential time, or finite time.

SUMMARY

It will be appreciated that a "knowledgebase" and "knowledge base" are distinctly different. A knowledgebase generally describes a database which can be searched via a search engine. The search engine for data in the database can obtain data without mandating (e.g., affirming) characteristics or relationships. In contrast, the knowledge base includes information within a context of an intelligent algorithm. The intelligent algorithm uses data with validated qualities and relationships. Thus, while the knowledgebase is merely a repository of data, which can be searched for the presence of specific data, the knowledge base is a domain library of specific knowledge (e.g., data with validated relationships) and/or data with imbedded relationship information.

An embodiment of a computer-implemented method for determining a disease state comprises a processor accessing from a computer-readable non-transitory memory, computer-readable data (e.g., knowledge base) representing a general graph (e.g., based on user-developed or a medical community's validated knowledge base) having nodes of physiological conditions (e.g., state, data, and/or features). Each of the physiological conditions is represented by each of the nodes, wherein each of the nodes is connected by one or more edges representing correlations between the nodes, the processor accessing from the computer-readable non-transitory memory, computer-readable data of physiological conditions of a patient, the processor executing computer-readable instructions for quantification of the physiological conditions of the patient, the processor transforming the physiological conditions of the patient to node data by performing quantification of the physiological conditions of the patient, the processor executing computer-readable instructions for associating the node data to the general graph, the processor creating an individualized graph by associating the node data to the general graph, the processor storing the individualized graph to the computer-readable non-transitory memory, the processor accessing from the computer-readable non-transitory memory, computer-readable data representing a topological module of nodes connected by edges, wherein the topological module represents the disease state (e.g., a computable surrogate of the disease state), and the processor executing computer-readable instructions for mapping the topological module to the individualized graph.

An embodiment of the computer-implemented method further comprises the processor mapping the topological module to the individualized graph, wherein the disease state is an emergent disease state.

An embodiment of the computer-implemented method further comprises the processor mapping the topological module to the individualized graph, wherein the disease state is a pre-emergent disease state.

An embodiment of a computer-implemented method for creating a graph for determining a disease state comprises storing on a computer-readable non-transitory memory, computer-readable data representing a general graph of physiological conditions, wherein each of the physiological conditions is represented as a node of the general graph, wherein each node is connected by one or more edges representing correlations between the nodes, and storing on the computer-readable non-transitory memory, computer-readable data representing a topological module of nodes connected by edges, wherein the topological module represents the disease state (e.g., a computable surrogate of the disease state), and the topological module can be mapped onto a portion of the general graph.

An embodiment of a computer-implemented method for determining a pre-emergent disease state comprises a processor accessing from a computer-readable non-transitory memory, computer-readable data representing physiological conditions represented as nodes, wherein at least one of the nodes has a correlation to another one of the nodes, the processor accessing from the computer-readable non-transitory memory, computer-readable data of first physiological conditions of a patient collected at a first time period, the processor transforming the first physiological conditions of the patient to first node data by performing quantification of the first physiological conditions of the patient, the processor accessing from the computer-readable non-transitory memory, computer-readable data of second physiological conditions of the patient collected at a second time period, the processor transforming the second physiological conditions of the patient to second node data by performing quantification of the second physiological conditions of the patient, the processor accessing from the computer-readable non-transitory memory, computer-readable data representing a topological module of nodes, wherein the topological module represents the pre-emergent disease state, the processor mapping the topological module to the first node data, the processor mapping the topological module to the second node data, and the processor determining the pre-emergent disease state based on the mapping the topological module to the first node data and to the second node data.

An embodiment of a medical general intelligence computer comprises a processor, and a computer-readable non-transitory memory in communication with the processor, the computer-readable non-transitory memory including and/or stored therein one or more processor-executable instructions for the processor to perform one or more of the computer-implemented methods disclosed herein.

An embodiment of a computer-implemented method for determining a disease state of a patient comprises a processor accessing from a computer-readable non-transitory memory, computer-readable data representing a general graph having nodes of physiological conditions, wherein each of the physiological conditions is represented by each of the nodes, wherein each of the nodes is connected by one or more edges representing correlations between the nodes; the processor accessing from the computer-readable non-transitory memory, computer-readable data of physiological conditions of a patient; the processor executing computer-readable instructions for quantification of the physiological conditions of the patient; the processor transforming the physiological conditions of the patient to node data by performing quantification of the physiological conditions of the patient; the processor executing computer-readable instructions for associating the node data to the general graph; the processor creating an individualized graph by associating the node data to the general graph; the processor storing the individualized graph to the computer-readable non-transitory memory; the processor accessing from the computer-readable non-transitory memory, computer-readable data representing a topological module of nodes connected by edges, wherein the topological module represents the disease state; the processor executing computer-readable instructions for mapping the topological module representing the disease state to the individualized graph; the processor executing computer-readable instructions for determining a weight averaged value of the node data of the topological module of nodes; the processor determining the disease state of the patient from the weight averaged value; the processor executing computer-readable instructions for creating a new general graph by replacing all of the nodes inside the topological module in the general graph with a super node of the weight averaged value; and the processor storing the new general graph to the computer-readable non-transitory memory.

The computer-implemented method can include the processor accessing from the computer-readable non-transitory memory, additional computer-readable data representing another topological module which includes the super node, wherein the topological module represents another disease state; the processor executing computer-readable instructions for mapping the another topological module representing the another disease state to the individualized graph; and the processor executing computer-readable instructions for determining another weight averaged value of the super node and other data of the another topological module.

The computer-implemented method can include the processor mapping the another topological module to the individualized graph, wherein the another disease state is an emergent disease state.

The computer-implemented method can include the processor mapping the another topological module to the individualized graph, wherein the another disease state is a pre-emergent disease state.

An embodiment of a computer-implemented method for determining a second disease state of a patient comprises a processor accessing from a computer-readable non-transitory memory, computer-readable data representing a general graph having nodes of physiological conditions and at least one super node representative of a first disease state, wherein each of the physiological conditions is represented by each of the nodes, wherein each of the nodes and the at least one super node is connected by one or more edges representing correlations between the nodes and at least one super node; the processor accessing from the computer-readable non-transitory memory, computer-readable data of physiological conditions of a patient; the processor executing computer-readable instructions for quantification of the physiological conditions of the patient; the processor transforming the physiological conditions of the patient to node data by performing quantification of the physiological conditions of the patient; the processor executing computer-readable instructions for associating the node data to the general graph; the processor creating an individualized graph by associating the node data to the general graph; the processor storing the individualized graph to the computer-readable non-transitory memory; the processor accessing from the computer-readable non-transitory memory, computer-readable data representing a topological module of nodes and at least one super node connected by edges, wherein the topological module represents the second disease state; the processor executing computer-readable instructions for mapping the topological module representing the second disease state to the individualized graph; the processor executing computer-readable instructions for determining a weight averaged value of the node data and the at least one super node of the topological module; and the processor determining the second disease state of the patient from the weight averaged value.

An embodiment of a medical general intelligence computer includes a processor; and a computer-readable non-transitory memory in communication with the processor, the computer-readable non-transitory memory including processor-executable instructions for determining a pre-emergent disease state of a patient, wherein when the processor executes the processor-executable instructions, the processor storing on the computer-readable non-transitory memory, computer-readable data representing a general graph of physiological conditions and at least one disease state, wherein each of the physiological conditions is represented as a node of the general graph, and the at least one disease state is represented as a super node of the general graph, wherein each of the nodes and the super node is connected by one or more edges representing correlations between the nodes and the super node; the processor storing on the computer-readable non-transitory memory, computer-readable data representing a topological module of the nodes and the super node connected by edges, wherein the topological module represents the second disease state, and the topological module can be mapped onto a portion of the general graph; and the processor storing on the computer-readable non-transitory memory, a weight averaged value of nodes and the super node of the portion of the general graph that has been mapped onto by the topological module for determining a second disease state.

BRIEF DESCRIPTION OF THE DRAWINGS

Referring now to the drawings in which like reference numbers represent corresponding parts throughout.

FIG. 11 illustrates an example of an emergent disease state vs. non-emergent disease state.

FIG. 12 illustrates an example of an individual's physiological data collected along a spatial and/or temporal dimension.

FIG. 13 illustrates an example of a chart showing a change in the disease intensity along a time dimension.

DETAILED DESCRIPTION

Figure 1:
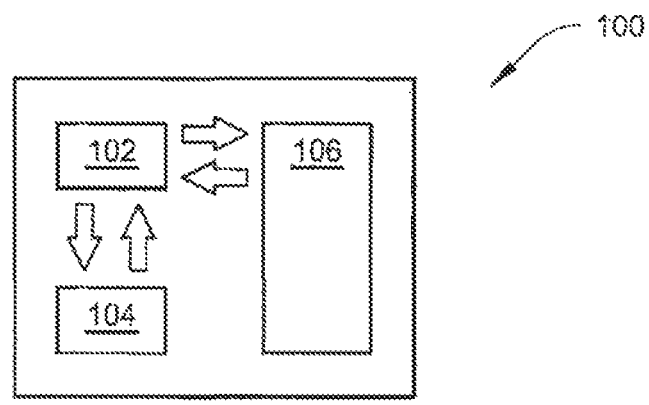
FIG. 1 illustrates a schematic box diagram of an embodiment of the Medical Reasoning System (MRS).

The embodiments disclosed are directed towards a computerized general intelligence systems applicable to the medical arts and a computerized method for determining risks associated with a medical diagnosis.

Generally, without a reproducible numerical descriptor, a particular complex disease state is difficult to define, predict, and/or manage. Generally, useable medical data (e.g., knowledge) for defining, predicting, and/or managing diseases are numerical values associated with morpho-physiologic features. Such numerical values are defined herein as morpho-physiological numbers. Examples of morpho-physiological features are, for example but not limited to, weight, heart rate, blood pressure, velocity, hemoglobin A1c, etc. Examples of morpho-physiological numbers are, for example but not limited to, 80 kg (weight), 50 beats per minute (heart rate), 160 mmHg (systole)/90 mmHg (diastole) (blood pressure), 5 meters/sec (velocity), 7.0% (Hemoglobin A1c) etc.

The morpho-physiological numbers are different from data rising out of a person's genetic makeup. That is, a person's genetic makeup (DNA) is generally a fixed micro-level blueprint which represents a genetic potential of the person. The person's genetic makeup does not represent the person's current physiological state at a macro-level and real world conditions. That is, it is impossible to determine whether the person is currently suffering from a disease state by looking only at a specific gene of that person. Multiple morpho-physiological features and numbers of the person must be determined and analyzed to determine whether the person is currently suffering from a particular disease and the state of that disease (e.g., clinical descriptor). The term physiological condition(s) is used herein to describe one or more physiological state, data, and/or feature(s).

General approaches to disease diagnosis have been based on observational correlations between pathological analysis and clinical data knowledge of the syndromes. General diagnostic tools show shortcomings of this methodology, reflecting both a lack of sensitivity identifying preclinical disease and lack of specificity in defining cause-and-effect. In addition, generally, diseases are principally studied by a trial-and-error process to figure out which treatment works for a given patient or pooled population.

Clinical descriptors such as "congestive heart failure", "cancer", "hypertension", etc. provide a name, or an identity, to a disease state. For example, a person with a blood pressure numbers (morpho-physiological numbers) of 160 mmHg (systole)/90 mmHg (diastole) can be determined to have clinical Arterial Hypertension, i.e., high blood pressure (clinical descriptor). However, a disease state of a biological system (e.g., animal, human, etc.) is rarely defined by a single physiological feature such as blood pressure. Instead, the disease state reflects perturbations of a complex physiological network of linked morpho-physiological features (e.g., tissues, organs, etc.). Thus, while the clinical descriptors are a convenient way of communicating in few words the complex perturbations of the physiological network, the clinical descriptors, by themselves, have not been able to provide sufficient information for numerical and/or computational analysis needed for determining cause-and-effect risk levels and/or management levels of perturbations of complex non-linear morpho-physiological features. That is, the clinical descriptors have been considered useless for numerical evaluations because the individual clinical descriptors are not reproducible numbers defining a dynamic complex biological state. For example, the clinical descriptor of "cancer" (of a patient who is suffering from cancer) has not itself been directly used for numerical and/or computational evaluation of the patient's current state of suffering from the disease, nor for determining risks of other related physiological conditions and/or disease states that the patient may suffer from in the near or distant future. That is to say, clinical descriptors (e.g., names of diseases or individual data features) were conceived for the sake of easily communicating complex physiological phenomenon between humans (e.g., knowledge based communication). Clinical descriptors have not been directly computable. Accordingly, clinical descriptors had not been used in determining and/or predicting individual risk levels of these perturbations of the morpho-physiological features. Additionally, clinical descriptors had not been used in determining and/or predicting an individual's emergent disease state and/or a pre-emergent disease state.

Disclosed herein are complex knowledge base systems and methods that define clinical descriptors as groupings of highly connected morpho-physiological features, such that the quantitative clinical descriptors can be used in determining and/or predicting risk levels (e.g., disease intensity) of these perturbations of the morpho-physiological features.

Disclosed herein are systems and methods that define clinical descriptors as a connection of morpho-physiological features, such that the clinical descriptors can be used in determining and/or predicting an emergent disease state and/or a pre-emergent disease state.

The systems and methods disclosed herein define clinical descriptors as quantifiable information. The systems and methods disclosed herein can describe clinical descriptors as multi-dimensional computer-readable data representing a topology of quantifiable morpho-physiological features.

The topology is described herein as a topological module. The morpho-physiological features are described herein as a network of nodes and/or hubs. The morpho-physiological numbers are described herein as numerical values for the associated morpho-physiological features (nodes and/or hubs). Accordingly, the topological module is a network representation (e.g., surrogate disease module) of connected nodes and/or hubs. Thus, clinical descriptors of diseases are represented as computer-readable data represented as a network connections and/or relationships of numbers associated with nodes and hubs. Accordingly, clinical descriptors, and a disease state, can also be visually represented as a graph having a network of connected nodes, wherein at least a portion of the graph can have a topological module of nodes connected by edges, wherein the topological module represents the disease state. Therefore, according to the embodiments herein, clinical descriptors can be numerically analyzed and computed. The graph is a connection of physiological conditions (e.g., data and/or features) represented as nodes, wherein each connection between the nodes represents a relationship between the two physiological conditions (e.g., causation, relation, association, correlation, etc.) based on user-developed or a medical community's validated knowledge base. The term "user-developer" describes a person who identifies the data and uses the knowledge base to transform the data relationship to intelligible information which can be processed by a processor.

A Medical Reasoning System (MRS) can be a specialized medical general intelligence computer configured to perform the computer-implemented methods disclosed herein. Embodiments of the MRS can have a processor and a computer-readable non-transitory memory in communication with the processor. The computer-readable non-transitory memory can store therein one or more processor-executable instructions for the processor to perform one or more of the computer-implemented methods disclosed herein.

FIG. 1 illustrates a box diagram of an embodiment of the MRS 100. The MRS 100 can be a specialized medical general intelligence computer configured to perform one or more of the computer-implemented methods disclosed above. The MRS 100 comprises one or more processor(s) 102, and a computer-readable non-transitory memory 104 in communication with the one or more processor(s) 102. One or more of the computer-readable non-transitory memory 104 stores therein one or more processor-executable instructions for the one or more processor(s) 102 to perform one or more of the computer-implemented methods disclosed above. The computer-readable non-transitory memory 104 can store one or more of computer-readable data, graph data, node data, node value, hub data, hub value, edge data, topological module data, individualized graph data, meta-data, and inference data. Examples of the computer-readable non-transitory memory 104 are non-transitory storage medium, such as but are not limited to, magnetic media (disc, film, ribbon, etc.), optical media (disc, film, ribbon, etc.), ROM, RAM, flash media, solid state drive, etc. The MRS 100 is configured with one or more Input/Output (I/O) device(s) 106 which is in communication with one or more of the processor(s) 102. Examples of the I/O device(s) 106 include but are not limited to a keyboard, a mouse, a touchscreen, a display device, etc. The I/O device(s) 106, such as the touchscreen and/or the display device, can display thereon a graphical user interface (GUI) for a user to interact with the MRS 100. The GUI can provide for displaying of information to the user and can receive user input via the user's interaction with the GUI.

The I/O device(s) 106 are device(s) configured to allow a user to interact with the MRS 100 and/or for the MRS 100 to interact with the user. Accordingly, one or more I/O device(s) 106 can provide for entering data (input), displaying data (output), displaying results of the analysis (output), etc.

An embodiment of the MRS 100 is configured to operate a computerized-method including an Artificial General Intelligence (AGI) method. The MRS 100 can analyze a topological module and morpho-physiological numbers for determining and/or predicting risk levels of perturbations of the morpho-physiological features. Further, the MRS 100 can analyze a topological module and morpho-physiological numbers for determining a risk of an emergent disease state. Further, the MRS 100 can analyze a topological module and morpho-physiological numbers for determining an emergent disease state. The MRS 100 can analyze a topological module and morpho-physiological numbers for predicting a pre-emergent disease state. Further, the MRS 100 can analyze a topological module and morpho-physiological numbers for determining a pre-emergent disease state. Further, the MRS 100 can analyze a topological module and morpho-physiological numbers for predicting a risk of a pre-emergent disease state.

An embodiment of the methods performed by the MRS 100 includes a medical application of the AGI method. The AGI methods described herein are directed to simplifying complex events. The AGI method can be applied to many different domains. Thus, the AGI method is domain-independent. That is, the AGI method includes domain-independent processing hardware and/or software, which can be applied universally and generally to all medical diagnostic and/or assistant methodologies. Further, the AGI method can be applied to obtaining and storing domain-specific knowledge (e.g., information, data, meta-data, etc.) using the general domain-independent methodology. The AGI methodology for obtaining and storing information does need to use a data search (e.g., iterative search algorithm). The AGI method does not attempt to replicate and/or compute every feature of a complex event. In contrast, the AGI method takes the features of the complex event, and simplifies the complex event to few features that are determined to be essential and/or important to that complex event. Accordingly, the AGI method allows for extremely fast computation and/or analysis of complex events.

The computer-implemented method including the AGI can integrate "autonomous learning," which is described herein to mean that the computer system can perform analysis of data without supervision by a person. The computer-implemented method including the AGI can integrate "goal-directed learning," which is described herein to mean that the computer system can perform selective analysis of data towards a goal set by the computer, without supervision by a person. The computer-implemented method including the AGI can integrate an "adaptive learning," which is described herein to mean that the computer system can perform cumulative and contextual analysis of data without supervision by a person. Adaptive learning can lead to additional data (e.g., new data).

The computer-implemented method including the AGI can include pattern recognition and pattern matching (e.g., mapping). Accordingly, the computer-implemented method including the AGI can include determining an inference between one set of data (wherein "set" can be one or more value(s)) to another set of data. An example of the inference between sets of data includes sets of data for same parameters taken at different times and disease types. The AGI method understand the concept of the time-dimension for these sets of data, and based on the changes in the sets of data, an inference data can be created as meta-data for the collective sets of the data.

The MRS 100 configured to perform the medical application of the AGI method can perform an analysis of data without the need to use disease-dependent language. That is, the MRS 100 can use data having disease-independent categorical language. The data used by the MRS 100 are formulated and associated in the terms and statements derived from experience-grounded semantics. That is, the formulations and the associations of the terms are pre-determined and determined based on experiences and/or behavior arising out of research (which a user inputs into and stored in the system memory) and/or self-learning (e.g., autonomous, goal-directed, and/or adaptive). An example of self-learning data includes but is not limited to inference rules of nodes determined by the system based on the data stored in the memory.

The embodiments disclosed herein are also directed to the MRS 100 and methods for performing an analysis (e.g., mapping) of one or more topological modules stored in the memory in comparison to the morpho-physiological numbers of nodes and/or hubs, determining a pre-emergent disease state (and/or risk(s) thereof). The embodiments can also provide an output for suggested management of particular morpho-physiological feature(s) for preventing and/or delaying an emergence of the pre-emergent disease state.

Figure 2:
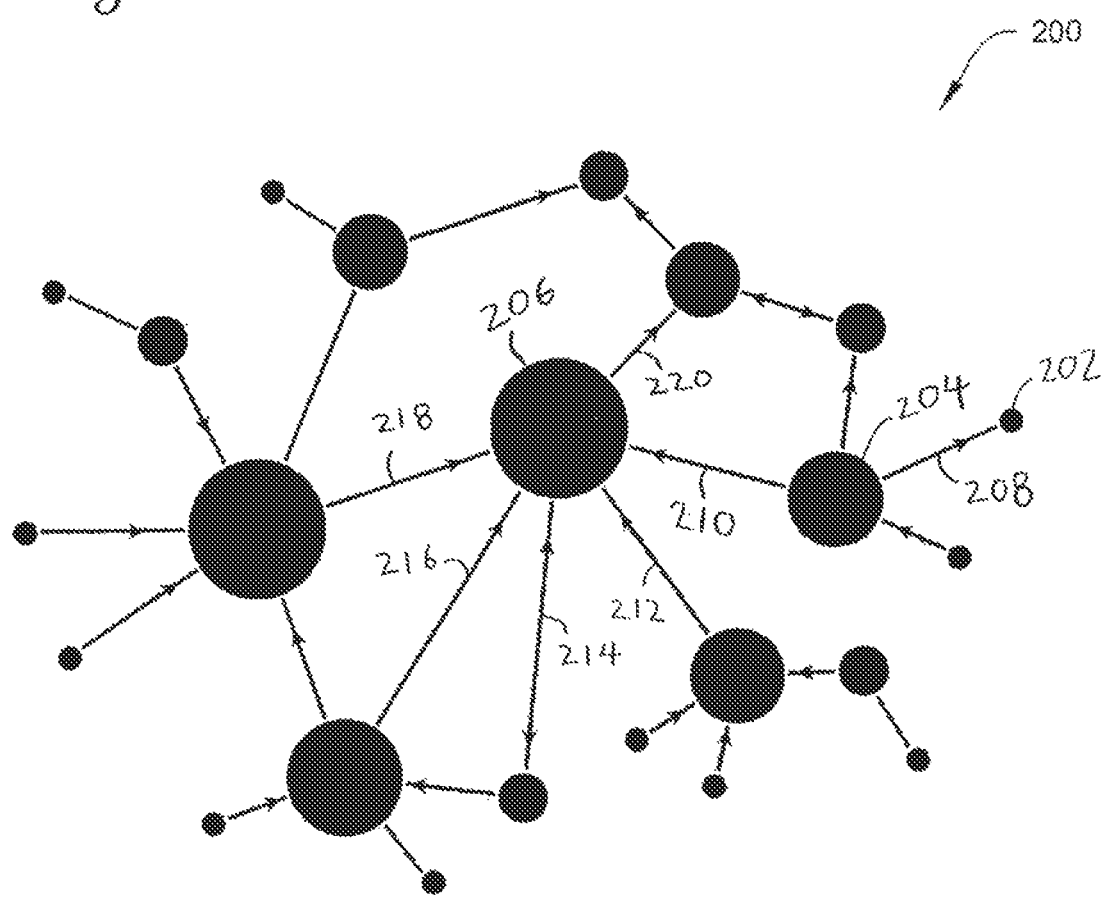
FIG. 2 illustrates an example of a graph, which is a visual (e.g., schematic) representation of data stored in a non-transitory memory of a MRS.

FIG. 2 illustrates an example of a graph 200 which is a visual (e.g., schematic) representation of data stored in a non-transitory memory (104 illustrated in FIG. 1) and processed by one or more processor(s) (102 illustrated in FIG. 1) of a MRS (100 illustrated in FIG. 1). The graph 200 is formed of a plurality of nodes (e.g., nodes 202, 204, 206) connected via edges (e.g., edges 208, 210, 212, 214, 216, 218, 220). Each edge 208, 210, 212, 214, 216, 218, 200 connects two nodes. The graph 200 includes nodes (e.g., node 202, node 204, and node 206) having different sizes to visually convey different relative magnitudes of connectivity for each of the nodes. For example, node 206, which has more connections than node 204, is represented in the graph 200 to have a larger size than the size of the node 204. The relative size variance of the nodes based on the magnitude of connectivity can enhance an easier understanding of the graph 200. For example, edge 208 connects nodes 202 and 204. A node can have one edge connected thereto (e.g., node 202 is connected to only one edge 208). A node can have multiple edges connected thereto (e.g., node 206 is connected to edges 210, 212, 214, 216, 218, 220). A node (e.g., 206) having more than a set number (e.g., a predetermined number) of edges connected thereto can be determined (e.g., identified, designated, etc.) to be a "hub." For example, if the set number is 4, then the node 206 can be determined to be a hub. For example, if the set number is 4, then the nodes 202, 204 can be determined to be "not hubs" (that is, the nodes 202 and 204 cannot be determined to be hubs). Each node 202, 204 and each hub 206 of the graph 200 can have a numerical value associated with it. The numerical value can be a value representative of a quantified (e.g., weighed measure) physiological condition of an individual. The graph 200 may be a general graph, which does not have numerical values (or the numerical values are null values) associated with each of the nodes 202, 204 and each of the hubs 206.

The MRS (100 illustrated in FIG. 1) can include a processor that can access a non-transitory memory for building information represented by the graph 200, modifying the information represented by the graph 200 by adding data that represent additional nodes, hubs, and/or edges, removing nodes, hubs, and/or edges, etc. Such modifications can be done by a user interacting with the MRS and/or self-learning by the MRS by appropriate analysis of other data. For example, if a new research shows that an association between node 202 and node 204 does not exist, then the processor of the MRS can access the non-transitory memory and remove the edge 208 associating the nodes 202, 204. This can be performed by the user purposefully interfacing with the MRS to remove the data representing the edge 208 of the graph 200, or the user can enter the change in the relational information between the two features that are represented as nodes 202, 204 and edge 208 (e.g., by interacting with the I/O device(s) 106 illustrated in FIG. 1), and the processor of the MRS automatically, and dynamically, changes the data representing the graph 200 accordingly (by removing the edge 208). Addition(s) of one or more of the nodes, hubs, and edges can also be performed by the user purposefully interfacing with the MRS (e.g., by interacting with the I/O device(s) 106 illustrated in FIG. 1), or the processor of the MRS automatically, and dynamically, changing the data representing the graph 200 according to new information the MRS has access to.

Each of the nodes 202, 204, 206 represents a computer-readable data (e.g., state) of a physiological feature (e.g., biological condition of a person, animal, etc.). Each of the edges 208, 210, 212, 214, 216, 218, 220 represents a relationship (e.g., association, causation, inference, etc.) between two physiological features (e.g., the nodes). For example, in the medical domain of cardiology, early diastolic velocity of the mitral valve annulus (e') and a ratio E/e' (wherein E is an early transmitral flow velocity) are related features. Thus, the node representing e' and the node representing E/e' would have an edge connecting them together. Also, the node representing E and the node representing E/e' would have an edge connecting them together. Further, because E/e' feature is related to left ventricular diastolic pressure (LVDP), a node representing E/e' would have an edge connecting to a node representing LVDP.

One or more processor(s) (102 illustrated in FIG. 1) can create a set of data which is representative of an individualized graph for a particular individual by populating the nodes of the graph 200 with numerical values representing the quantified (e.g., weighed measure) physiological condition of the individual. The numerical values may be a scaled value (e.g., 1 to 4), wherein the scaled value is a translation of real measured value. The processor(s) can store the individualized graph to the memory of the MRS. For example, when the processor(s) receives an individual's physiological data for e' and E, the processor(s) can populate the respective nodes for e', E, and E/e' with the physiological data and/or scaled values representing the received physiological data based on a set ranges (stored in the memory) for the respective physiological features. Accordingly, the processor(s) can create the individualized graph for the particular individual by populating the nodes e', E, and E/e' with quantifiable numerical values. The processor(s) can determine not to populate one or more of nodes of the graph 200 with one or more of the received physiological data when creating the individualized graph. Such determination can be made by the processor(s) when the physiological data includes information for a node that represents a less important feature (e.g., has only one edge connected to another node (which is not a hub)).

Figure 3:
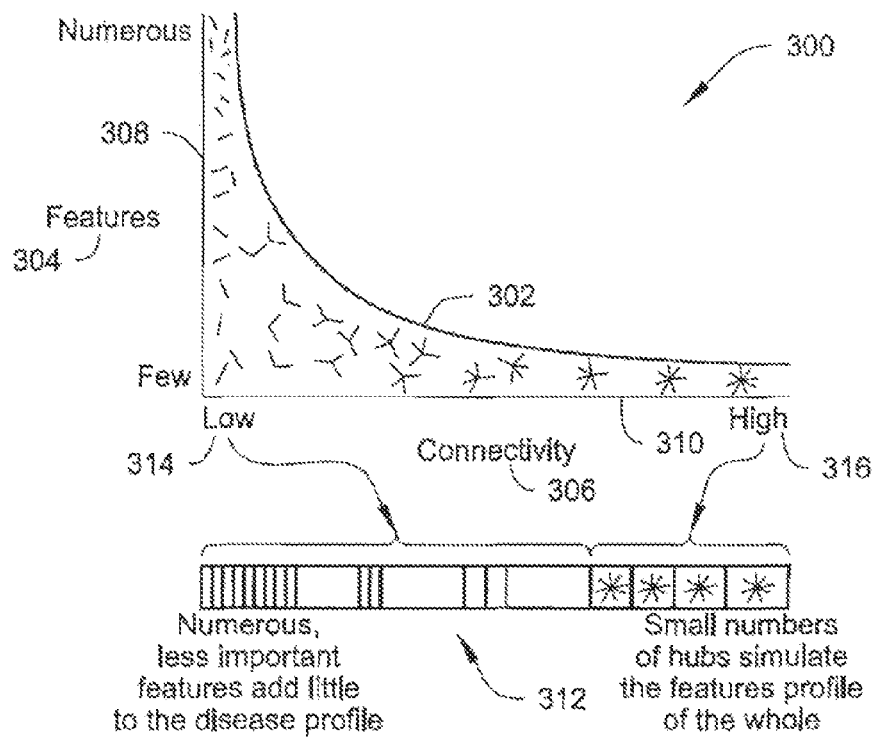
FIG. 3 illustrates an example of a complex relationship view of a graph (of a power function distribution) between physiological features (e.g., nodes) and their connections (e.g., edges).

FIG. 3 illustrates an example of a complex relationship 300 view of a graph (e.g., graph 200 illustrated in FIG. 2) between physiological features (e.g., nodes) and their connections (e.g., edges). The curve 302 represents a power law relationship (e.g., distribution) between the physiological features 304 and their interconnectivities (e.g., connectivity) 306. The Y-axis 308 represents the number of quantifiable physiological features 304. The X-axis 310 represents the number of connectivity 306 that exist between the features. According to the power law curve 302 (e.g., power law distribution), there are very few quantifiable physiological features 304, which have high connectivity 306. Dimensionally compressed view 312 of the curve 302 shows that there are many features (nodes) 314 with few connections, and that there are a small number of features (hubs) 316 with high number of connections. The power law distribution is scale free (e.g., random removal of a large number of the less connected nodes will not disturb the network while removal of highly connected hubs will markedly disturb the network system). Taking out the highly connected hubs will break the network system.

Figure 4:
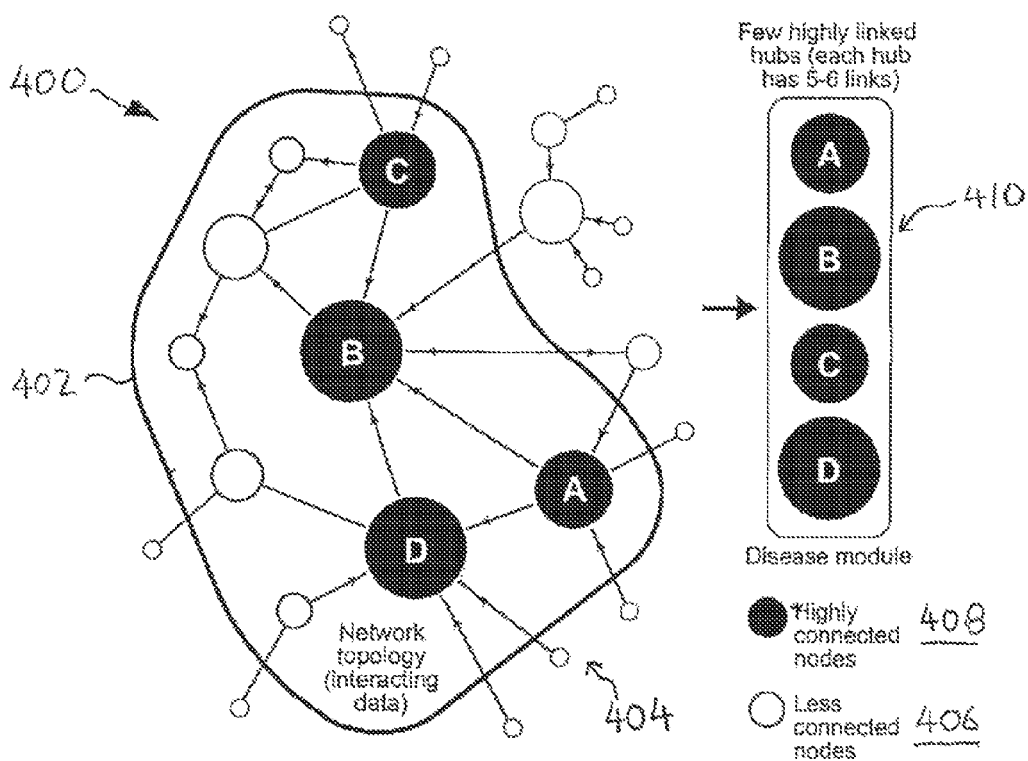
FIG. 4 illustrates an example of a visual (e.g., schematic) representation of an analysis process carried out by the MRS.

FIG. 4 illustrates a visual (e.g., schematic) representation 400 of an analysis process (e.g., mapping) carried out by one or more processor(s) (102 illustrated in FIG. 1) of the MRS (100 illustrated in FIG. 1), wherein a clinical descriptor has been transformed into a topological module 402.

The MRS can represent one or more clinical descriptors (diseases) as quantifiable association of physiological features and quantifiable data. That is, the MRS can transform and store clinical descriptors of diseases as computer-readable data, wherein the computer-readable data represent a network of connections and/or relationships of numbers (e.g., states) associated with nodes and hubs. Accordingly, as illustrated in FIG. 4, clinical descriptors and a disease state can be visually represented as a topological module 402 having a network of connected nodes.

The topological module 402 has been mapped onto a graph 404 in the visual (e.g., schematic) representation 400.

Although the visual representation 400 can be displayed on a computer and/or MRS, it will be understood that the visual representation 400 can be stored and processed by the MRS and does not necessarily exemplify what must be displayed and/or shown on a display device (of the computer and/or MRS). The mapping illustrated in FIG. 4 can be performed by pattern recognition and/or pattern matching method performed by the processor of the MRS. For the visual (e.g., schematic) representation 400, the topological module 402 is indicated by a border (e.g., surface created by a network of nodes and edges representing the topological module 402). The topological module 402 represents a group of nodes wherein their perturbations are validated to be linked to a particular disease. The topological module 402 has nodes (features) that are considered to be necessary to specific disease states. The MRS employing the AGI method can segregate non-essential nodes and removes them from consideration (computational analysis does not include non-essential nodes). For example, the topological module 402 includes a network of nodes that are less connected 406 (shown as open circles). The topological module 402 includes nodes that are highly connected 408 (shown as filled-in circles). The MRS employing the AGI method can segregate the less connected nodes 406 (shown as open circles) as non-essential nodes of the topological module 402 and need not consider them for further analysis of making a medical determination and/or prediction associated with the topological module 402 and an individual's physiological data. Only the highly connected nodes 408 (A, B, C, D) of the topological module 402 can be considered. The term highly connected means that the number of edges connected to a node is greater than a set number. In this example, the set number is four. Each of the highly connected nodes 408 (A, B, C, D) have number of edges connected thereto that is greater than four. The set number can be changed as needed and/or desired by the MRS and/or a user.

The processor of the MRS can create a disease module 410 into memory, represented by the highly connected nodes 408 (A, B, C, D). However, the MRS need not create a separate module 410 from the topological module 402. Further analysis can be performed using the topological module 402, but considering only the highly connected nodes 408 (ignoring the less connected nodes 406), instead of creating a separate disease module 410 into memory. Accordingly, the terms topological module and disease module can be used interchangeably, wherein the term disease module defines a subset of domain specific highly connected nodes of the topological module of a disease state. Accordingly, the disease module 410 can be viewed as a breakdown or simplification of the topological module 402.

Further, the highly connected nodes 408 can be defined to be a macro node. The macro node is used herein to mean a network of the fewest number of the most highly connected disease associated nodes. Accordingly, the macro node can represent a single quantifiable measure of a feature-to-disease expression. For each clinical descriptor, a macro node can be determined by the above process. The macro nodes can be stored into the memory of the MRS. The macro nodes can be used in a quantifiable inference process to compute the dynamical integrity (coherence, intensity, variance, etc.) of a particular emergent disease.

Figure 5:
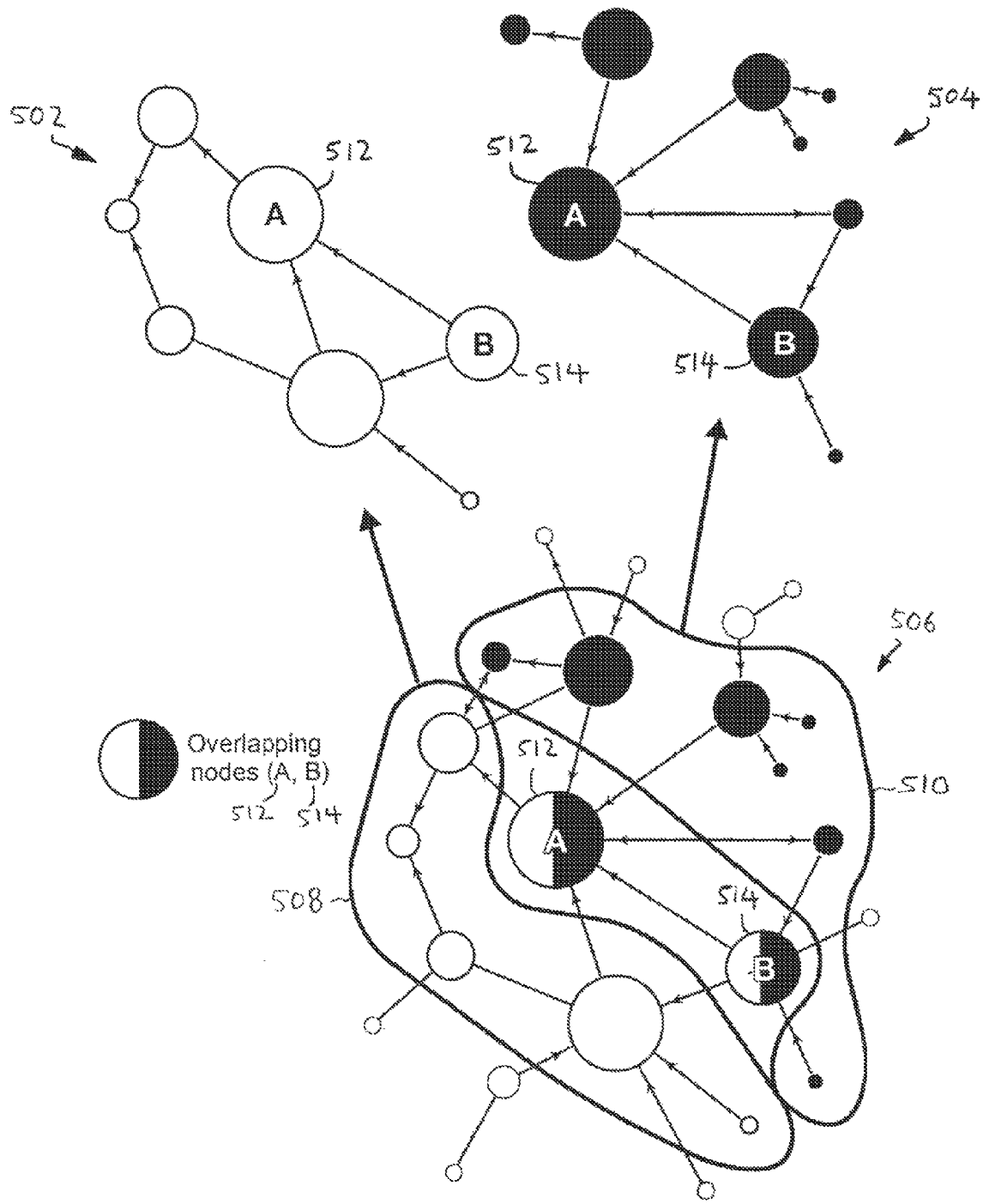
FIG. 5 illustrates examples of topological modules.

FIG. 5 illustrates examples of topological modules 502, 504 which can be mapped onto a graph 506. Each of the topological modules 502, 504 represents a disease state (e.g., clinical descriptor). The MRS (100 illustrated in FIG. 1) can map one or more of the topological modules 502, 504 onto the graph 506. The MRS can determine that at least a portion of the graph 506 represents one or more topological modules 508, 510 by, for example, pattern matching and/or pattern recognition. Accordingly, the topological module 502 has the same network structure as the topological module 508 mapped onto graph 506. Further, the topological module 504 has the same network structure as the topological module 510 mapped onto graph 506. When viewed separately, the topological modules 502, 504 do not necessarily convey any information about their association. However, when the topological modules 502, 504 are mapped onto the graph 506 as topological graphs 508, 510, the MRS can determine that the topological graphs 508, 510 have overlapping nodes "A" 512 and "B" 514. Further, the topological modules 502, 504 viewed separately may not necessarily convey the information that the nodes (A 512, B 514) are both highly connected nodes, because each of these nodes 512, 514 in the topological modules 502, 504 have only three edges connected thereto. However, when mapped onto the graph 506 as topological graphs 508, 510, the MRS can determine that the overlapping nodes (A 512, B 514) are both highly connected nodes (e.g., these nodes 512, 514 are hubs) for both topological modules 508, 510. Accordingly, by the mapping process, the MRS can determine that there is an inference relationship, represented by the overlapping nodes (A 512, B 514) between the two disease states represented by the topological modules 502, 504.

Figure 6:
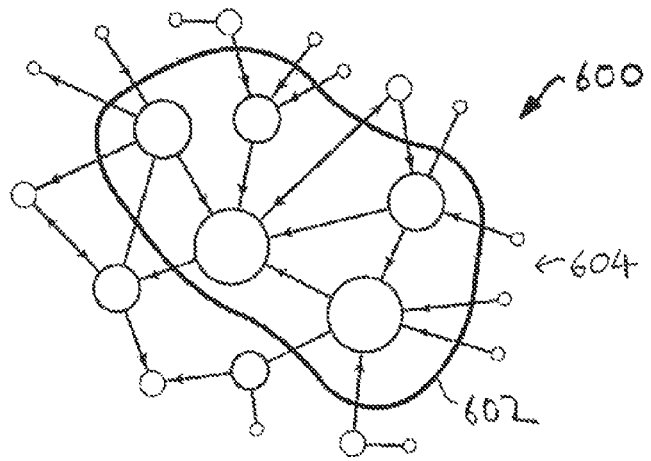
FIGS. 6-8 illustrate an example of an embodiment of the Artificial General Intelligence (AGI) method.
Figure 7:
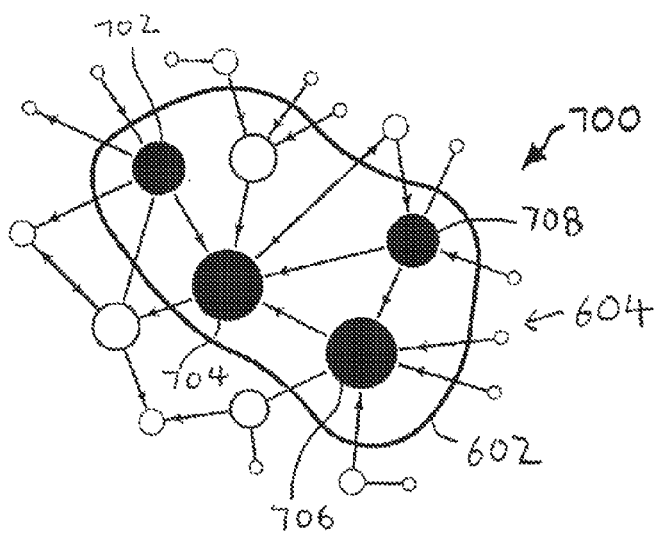
Figure 8:
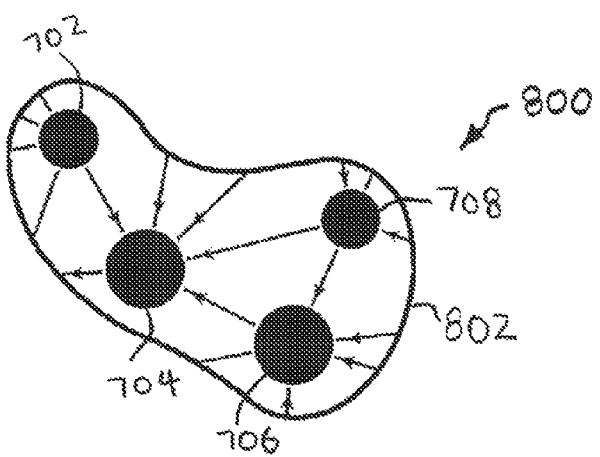

FIGS. 6-8 illustrate an embodiment of the AGI method, which can be performed by the MRS (100 illustrated in FIG. 1) for simplifying a complex network of physiological features to few highly connected hubs for making an inference between two sets of topological modules.

FIG. 6 illustrates a visual (e.g., schematic) representation 600 of a topological module 602 of a disease state (e.g., emergent disease) mapped onto a graph 604 (which has the same topology as the graph 404 illustrated in FIG. 4 with respect to nodes and edges connecting the nodes).

FIG. 7 illustrates a visual (e.g., schematic) representation 700 of the topological module 602, wherein overlapping nodes 702, 704, 706, 708 (filled-in circles) of the topological module 602 and another topological module (i.e., 402 illustrated in FIG. 4) are shown. Although not shown in FIG. 7, FIG. 4 shows the module 402 having the highly connected nodes 408 labeled as A, B, C, and D.

FIG. 8 illustrates a visual (e.g., schematic) representation 800 of a portion of the graph (604 illustrated in FIGS. 6 and 7) showing only the inference nodes 702, 704, 706, 708. These inference nodes 702, 704, 706, 708 can be defined to be a macro node 802 for the two topological modules (402 illustrated in FIGS. 4 and 602 illustrated in FIG. 6). That is, the macro node 802 is a network of the fewest number of the most highly connected disease associated nodes 702, 704, 706, 708 for both topological modules (402 illustrated in FIGS. 4 and 602 illustrated in FIG. 6). Accordingly, the AGI method carried out by the MRS can determine that the same macro node 802 exists for the disease states represented as topological modules (402 illustrated in FIGS. 4 and 602 illustrated in FIG. 6). This inference relationship data can be stored into the memory of the MRS. The macro node 802 and inference relationship data can be used in an inference process to determine an emergent disease and pre-emergent disease. For example, if the topological module 402 (illustrated in FIG. 4) is an emergent disease, and the topological module 602 (illustrated in FIG. 6) is a pre-emergent disease, the inference nodes determined by the MRS allows the MRS to predict that the emergence of the disease represented by the topological module 402 (illustrated in FIG. 4) means that the disease represented by the topological module 602 (illustrated in FIG.

6) will or is highly likely to emerge. Numerical analysis of the node values can be performed by the MRS to calculate the risks of the emergence of pre-emergent disease state represented by the topological module 602 (illustrated in FIG. 6).

Figure 9:
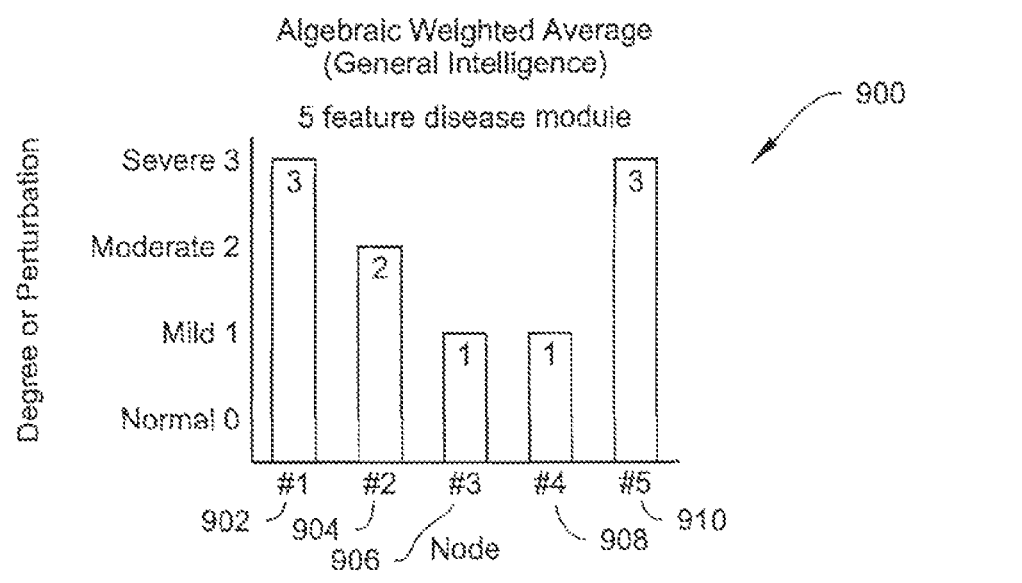
FIG. 9 illustrates an example of the numerical analysis of node values, which can be performed by the MRS.

FIG. 9 illustrates an example of the numerical analysis of node values which can be performed by the MRS. The data/features contained within a disease module are typically non-linear and vacillate among various state weights. A disease is rarely a consequence or reflection of a single data/feature but reflects the perturbations of a complex network that links multiple data/features. Disease module behavior is not random but a series of general organizing principals in their structure and evolution. Data/feature nodes are interdependent and continuously readjust in order to stabilize their integrated state.

FIG. 9 shows a chart 900 for performing a numerical analysis of values for five nodes 902, 904, 906, 908, 910. For example, the nodes 902, 904, 906, 908, 910 can be hubs of a topological module for a disease state. The topological module may be mapped onto a graph, wherein each of the nodes 902, 904, 906, 908, 910 has physiological data of an individual for creating an individualized graph.

A scaled value is assigned by the MRS for the physiological data for each of the nodes 902, 904, 906, 908, 910. That is, each node 902, 904, 906, 908, 910 represents a group of highly connected physiological features that represent a disease state, and physiological data has been received by the MRS. The MRS scales the physiological data for each of the physiological features (nodes 902, 904, 906, 908, 910) and assigns the scaled value to the nodes 902, 904, 906, 908, 910. The scaled values can be, for example but not limited to, integer values from 0 to 3, wherein 0=normal, 1=mild, 2=moderate, 3=severe. The scaled values represent a degree of perturbation for each of the physiological feature (node 902, 904, 906, 908, 910).

The chart 900 shows that the physiological data of the individual for the physiological feature (node 902) is severely perturbed from normal (scaled value=3).

The chart 900 shows that the physiological data of the individual for the physiological feature (node 904) is moderately perturbed from normal (scaled value=2).

The chart 900 shows that the physiological data of the individual for the physiological feature (node 906) is mildly perturbed from normal (scaled value=1).

The chart 900 shows that the physiological data of the individual for the physiological feature (node 908) is mildly perturbed from normal (scaled value=1).

The chart 900 shows that the physiological data of the individual for the physiological feature (node 910) is severely perturbed from normal (scaled value=3).

The MRS can calculate a Total module weight 912 from the scaled values of the five nodes 902, 904, 906, 908, 910. For example, the Total module weight 912 can be a sum of the scaled values of the five nodes 902, 904, 906, 908, 910, which is 10. A maximum modular weight value can be determined based on the number of nodes in the topological module and the maximum scale value (in this example, 3) for each node. The maximum modular weight is a value represented by the maximum scale value (in this example, 3) multiplied by the number of nodes (in this example, 5). Thus, in this example, the maximum modular weight is 3×5=15.

The MRS can calculate a Variance 914 of the individual's physiological data from normal by, for example, dividing the Total module weight 912 (value of 10) by a maximum modular weight (value of 15). This ratio is the Variance 914. Accordingly, the Variance 914 can be a real number scaled from 0.0 to 1.0, wherein 0.0 represents absolute normalcy, and 1.0 represents severe variance from normal. Another form of numerical scale may be used. In this example, the Variance 914 is 10/15=0.67. That is, the physiological state of this individual has a Variance 914 from normal of 0.67. Accordingly, a single numerical value can be used in quantifying numerically and computationally determining perturbations and variance of an individual's physiological state from normal with respect to a clinical descriptor (disease state). In this example, the Variance 914 of 0.67 would indicate a "moderate" clinical state 916 in relation to the disease state represented by the nodes 902, 904, 906, 908, 910. An inference state 918 is a value determined by the maximum scaled value multiplied by the weight average value. The inference state 918 is related to a probability of an event given the occurrence of another event. That is, the inference state 918 value can be used in determining a quantifiable risk of emergence of another disease state. In this example, the maximum scaled value is 3, and the weight average value is 0.67. Thus, the inference state 916 value is 3×0.67=2.1. The steps in the process illustrated in FIG. 9 and described in relation to FIG. 9 are performed by the MRS.

Figure 10:
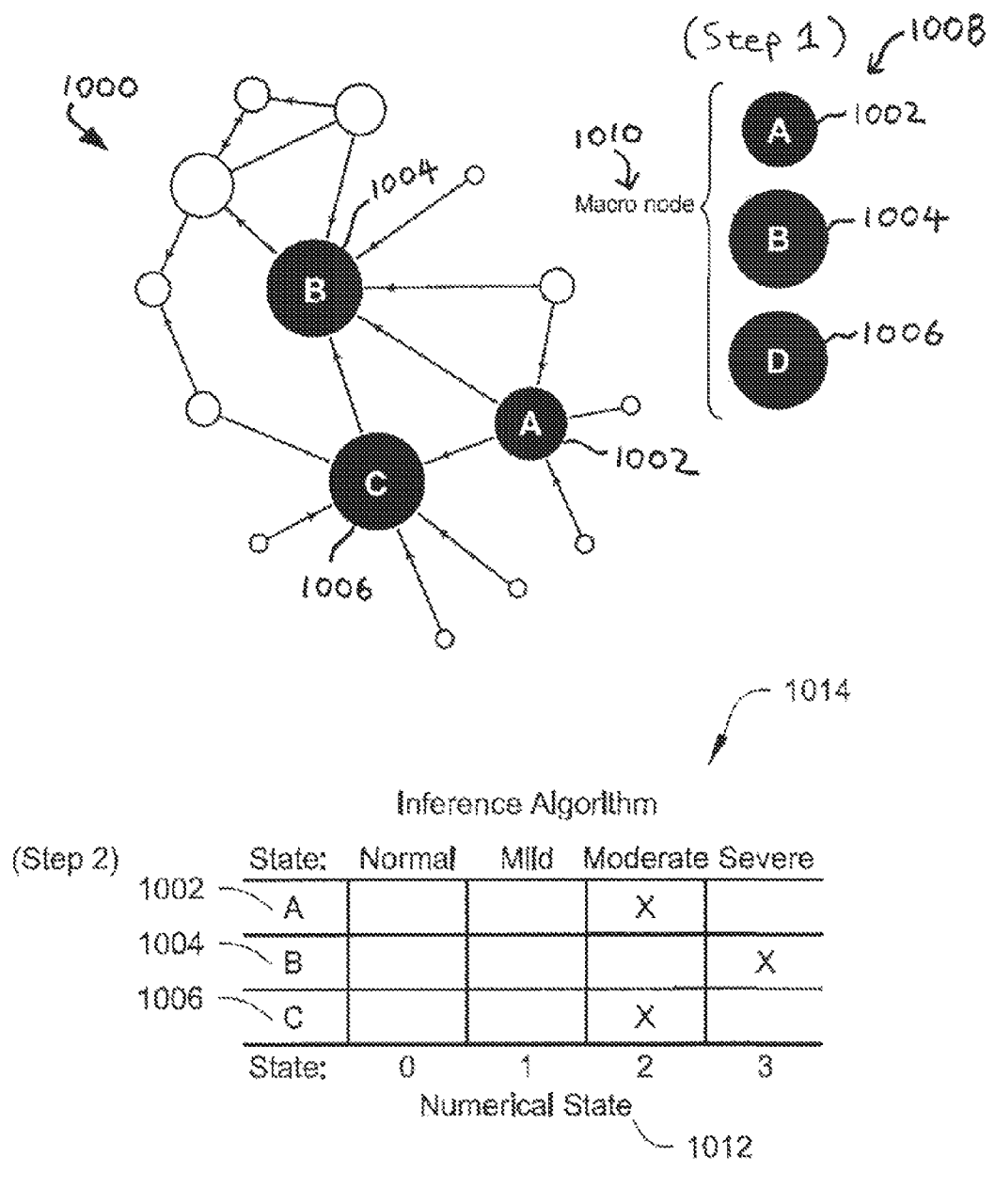
FIG. 10 illustrates an example of the steps carried out by the MRS using the AGI method.

FIG. 10 illustrates another example of the steps carried out by the MRS using the AGI method.

In Step 1, the MRS performs a node aggregation step to a network of nodes, reducing the total network (e.g., graph) using node aggregation into a small singly connected graph 1000. The MRS identifies a macro node, or a set of fewest highly connected nodes 1002, 1004, 1006 (e.g., hubs) in the graph 1000. The MRS can computationally represent these hubs 1002, 1004, 1006 as an aggregated set of features (A, B, C) 1008 forming the macro node 1010.

In Step 2, the MRS transforms the graph 1000 into a scaled value (e.g. numerical state) 1012 for each hub 1002, 1004, 1006, wherein each of the scaled value represents a clinically equivalent range for the physiological feature represented by the hub 1002, 1004, 1006. For example, the scaled values can represent qualitative states 1014 of normal, mild, moderate, and severe.

In the example shown, the physiological features represented by nodes A 1002 and C 1006 are determined by the MRS to be "moderate" and to have the scaled values of 2. The physiological feature represented by node B 1004 is determined by the MRS to be "severe" and to have the scaled value of 3.

In Step 3, the MRS determines that the number of hubs 1002, 1004, 1006 defining the disease state (topological module) is 3 1016, the summed group state is 7 (e.g., 2+2+3) 1018, the maximum state of the disease state is 9 (e.g., physiological condition of an emergent disease state) 1020, and the current condition value in relation to the disease state is 0.78 (e.g., summed group state divided by the maximum state=7/9=0.78) 1022. This current condition value infers the magnitude of variance from normal in relation to the disease state represented by the topological module defined by the hubs 1002, 1004, 1006.

Following are examples of hubs of a macro node, which defines a disease state, and clinical ranges of the physiological data for the qualitative states of normal, mild, moderate, and severe. The qualitative states of normal, mild, moderate, and severe can be assigned scaled values of 0, 1, 2, and 3, respectively. The following multi-domain examples and many other topological modules can be stored in the memory of the MRS. The MRS can receive patient data having physiological data for the following features, apply the AGI method described herein, and determine and/or predict the related emergent disease state and/or pre-emergent disease state. The MRS can receive patient data having physiological data for the following features, apply the AGI method described herein, and determine a risks for the related pre-emergent disease states from becoming emergent.

EXAMPLE 1

Endocrinology

| Disease State: Diabetes | | | | |
|---|---|---|---|---|
| Hub | Normal | Mild | Moderate | Severe |
| Hgb A1c % | <5.7 to 6.4 | ≥6.4 to 7.5 | >7.5 to 8.5 | >8.5 |
| GFR Glomerular filtration rate mL/min/1.73 m² | ≥70 | 70 to 50 | 50 to 30 | <30 |
| Hemoglobin gm/dL | 13.8 to 17.2 M 12.1 to 15.1 F | <12 | 12 to 10 | <10 |
| Weight (BMI) | <25.0 | 25.0 29.9 | 30-39.9 | ≥40 |

EXAMPLE 2

Gastroenterology

| Disease State: Celiac Disease | | | |
|---|---|---|---|
| Hub | Normal | Mild Moderate | Severe |
| TTG antibody Test (anti-transglutaminase antibodies) | Negative | Variable | Positive 10X abnormal |
| EMA-IgA Anti-endomysial antibody | Negative | Variable | Positive |
| HLA Genetic Tissue Type (human leukocyte antigen | Negative | Variable | Positive (30% over diagnosis) |
| Small Bowel Biopsy | Negative | Sampling Error Variable | Positive |

EXAMPLE 3

Hepatology

| Disease State: Light Chain Amyloidosis | | |
|---|---|---|
| Hub | NORMAL or ABSENT | PRESENT |
| Serum-Immune Fixation | Yes/No | Yes/No |
| Urine-Immune Fixation | Yes/No | Yes/No |
| Free Immunoglobulin Light Chain Kappa/Lambda ratio | >1/3 ratio | >3 ratio |

EXAMPLE 4

Oncology

| Disease State: Pancreatic Cancer | | | | |
|---|---|---|---|---|
| Hub | Normal | Mild | Moderate | Severe |
| CA 19-9 (carbohydrate antigen 19-9) Cancer antigen 19-9 | 37-50 | >100 | | |
| Chronic Epigastric Pain | None | Mild intermittent | | Chronic Severe |
| Jaundice | None | Document Screening | | |
| CT Image of an epigastric mass | None | Positive (Possible) | | Positive (Definite) |

EXAMPLE 5

Pulmonology

| Disease State: Obstructive Airway | | | | |
|---|---|---|---|---|
| Hub | Normal | Mild | Moderate | Severe |
| FEV1/FVC ratio | <70% | | >70% | |
| Total Lung Capacity | >80% | 60-80 | 50-50 | <50% |
| Residual Volume (RV/TLC ratio) | ≤100 | | | 150 |
| DLC Diffusing Lung Capacity | >80% | | <30% | |

EXAMPLE 6

Rheumatology

| Disease State: Rheumatoid Arthritis | | | | |
|---|---|---|---|---|
| Hub | Normal | Low | Moderate | High |
| Tender Joints | 0 | — | — | 28 |
| Swollen Joints | 0 | — | — | 28 |
| Sedimentation Rate (mm/hr) | 0-15 0-20 men 0-20 0-30 fem | — | — | — |
| C-Reactive Protein-hs mg/L | <1.0 | <3.0 | — | — |
| Pain Scale (%) | 0 | — | — | 100 |
| Global Patient Scale (%) | 0 | — | — | 100 |
| Global Physician Scale (%) | 0 | — | — | 100 |

FIG. 11 illustrates how the MRS determines and differentiates between an emergent disease state vs. non-emergent (or pre-emergent) disease state. In Status A 1100 and Status B 1102, the hubs (e'=myocardial relaxation; E/e'=filling pressure; LAVI=chronicity of filling pressure; E/A and DT=acuity of filling pressure) for heart failure state are provided. The MRS reads the hubs 1104 from the memory of the MRS and processes physiological data received by the MRS, and determines the quantitative and qualitative state for each of the hubs 1104. In State A 1100, the qualitative states for the hubs 1104 are e'=moderate, E/e'=mild, LAVI=moderate, E/A=moderate, and DT=moderate. The MRS can perform the AGI method of quantitative determination of variance and conclude that the received physiological data in Status A 1100 is asymptomatic. That is, Status A 1100 is determined to have non-emergent disease for heart failure.

In contrast, for Status B 1102, the MRS reads the hubs 1104 from the memory of the MRS and processes a different (either of another individual from Status A, or from the same individual as Status A but at a different time) physiological data received by the MRS, and determines the quantitative and qualitative state for each of the hubs 1104. In State B 1102, the qualitative states for the hubs 1104 are e'=moderate, E/e'=severe, LAVI=severe, E/A=severe, and DT=severe. The MRS can perform the AGI method of quantitative determination of variance and conclude that the received physiological data in Status B 1102 has an emergent disease, e.g., heart failure.

FIG. 12 illustrates an example of an individual's physiological data 1200 collected along a time dimension (e.g., data has been collected many times at different times). The hubs 1202 (Left atrial volume index LAVI, Tissue Doppler myocardial relaxation e', Left ventricular filling pressure E/e', Mitral valve deceleration time DT, Mitral valve MV) define the disease state of Atrial Fibrillation. At one point in time, the MRS has determined, based on the analysis of the values for the hubs 1202, that the individual does not have an emergent Atrial Fibrillation disease state. For example, the qualitative states of the hubs 1202 for time 1204 are all normal.

Yet, at another point in time 1206, the MRS has determined, based on the analysis of the values for the hubs 1202, that the individual does have an emergent Atrial Fibrillation disease state. For example, the qualitative states of the hubs 1202 for time 1206 are LAVI is abnormally large, e' is abnormally low, E/e' is highly variable, MV and DT are both abnormally variable. The MRS can determine during the time period 1208 that the individual is heading towards the emergent condition shown at time 1206. Periodic measurements of the physiological data for the hubs 1202 during the time 1206 received by the MRS can be used in determining the total variance value (or disease intensity). As described above (for example, FIG. 9), the disease intensity is a single numerical value (per taking of a physiological data), which can be used in quantifying numerically and computationally determining perturbations and variance of an individual's physiological state from normal with respect to a disease state. This disease intensity (e.g., weighted degree of variance) value can be measured at different times, and the MRS can determine a trend in the change of the disease intensity value.

For example, FIG. 13 shows a chart 1300 showing a change in the disease intensity 1302 (Y-axis) along a time dimension 1304 (X-axis). The MRS can determine the intensity state 1302 of two disease modules (e.g., chronicity 1306 and acuity 1308) over the time dimension 1304. The MRS calculates and stores disease intensity values of the disease modules 1306, 1308. The MRS can infer a relationship between the two disease modules 1306, 1308 because the change in the data for the two disease modules along the time dimension shows an interdependence phenomenon. Chronicity (historical burden of left ventricular filling pressure) and acuity (burden of filling pressure at the time of data acquisition) can be drawn as a chart 1302 along the time dimension 1304 (the MRS can computationally determine this relationship without necessarily graphing the chart 1304). The acuity 1308 evolves to a lower degree of intensity and chronicity to a higher degree of intensity. Based on the time dependent changes the MRS can provide an output via the I/O device(s) for a user so that the user can appreciate the interdependency of data and make a more informed management decision.

Figure 14:
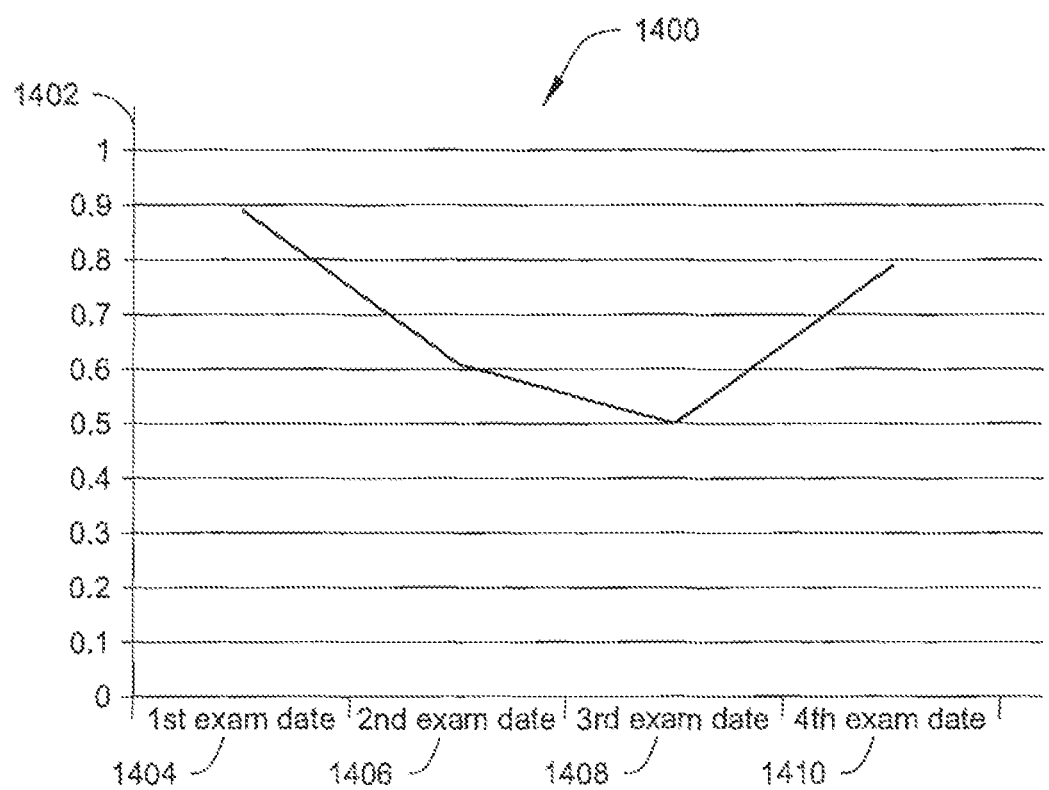
FIG. 14 illustrates an example of a chart resulting from the MRS performing a metadata analysis of temporal data.

FIG. 14 illustrates an example of a chart 1400 resulting from the MRS performing a metadata analysis of temporal data, for the disease Heart Failure, using hubs e', LAVI, E/e', DT, and E/A. The MRS determines a disease intensity (or variance) from a numerical analysis using the AGI method for an individual's physiological data in relation to a disease module. The chart 1400 includes a disease intensity 1402 (Y-axis) having a value of 0 (normal) to 1 (severe). The chart 1400 has the time dimension along the X-axis. Thus, the MRS determines a first disease intensity 1404 for a 1st exam date. The MRS determines a second disease intensity 1406 for a 2nd exam date. The MRS determines a third disease intensity 1408 for a 3rd exam date. The MRS determines a fourth disease intensity 1410 for a 4th exam date. A table of the disease intensities is shown in the table below. Further, based on the differences between the disease intensities, the MRS can determine qualitative information as to whether the individual is improving or deteriorating over time.

|  | 1st exam date | 2nd exam date | 3rd exam date | 4th exam date |
| --- | --- | --- | --- | --- |
| Disease Intensity Change | 0.89 Beginning | 0.61 Improve | 0.5 Improve | 0.79 Deteriorate |

Accordingly, the MRS metadata analysis is capable of exhibiting a robust expression of disease status and tracking of management decisions.

The MRS can predict (e.g., cause-and-effect), based on the quantified numerical analysis (e.g., weighted averaging) using the AGI method of processing hubs related to a topological module and emergent conditions, one or more events that are pre-emergent. Further, based on the predicted events, the MRS can provide an output via I/O device(s) of a suggested physiological and/or medical management/treatment for preventing and/or altering and/or delaying the emergence of the predicted event.

The table below provides some examples of the MRS making a determination of an emergent condition, predicted event(s), and suggested management output (e.g., disease management based on surrogate cause-and-effect modeling).

| Hubs (features) | = | Emergent Condition | = | Predicted Event(s) | = | Suggested Management Output |
| --- | --- | --- | --- | --- | --- | --- |
| Blood Pressure + Cardiac Dysfunction | = | Hypertensive Heart Disease | = | Stroke, Heart Failure, Renal Failure, etc. | = | Medical Management |
| Ejection Fraction + Systolic myocyte excursion (fibrosis) + wall motion | = | Systolic Cardiac Dysfunction | = | Heart Failure, Coronary Artery Disease | = | Medical/Surgical Management |

-continued

| Hubs (features) | = | Emergent Condition | = | Predicted Event(s) | = | Suggested Management Output |
|---|---|---|---|---|---|---|
| Myocyte relaxation + elevation LV filling pressure | = | Diastolic Cardiac Dysfunction | = | Stroke, Congestive Heart Failure | = | Medical Management |
| Multivariable echo/ Doppler hemodynamic profile | = | Valve Disease | = | Stroke, Heart Failure, Death | = | Medical/Surgical Management |
| Myocardial relaxation (e') + chronicity of LV filling pressure | = | Atrial Fibrillation | = | Stroke, Heart Failure, Death | = | Medical/Surgical Management |

The MRS can proceed with assisted and/or autonomous learning based on the graph, topological modules, and physiological data received and stored in the memory of the MRS. For example, where the MRS performs variance determinations based on hubs of a particular topological module, the MRS can include one or more nodes (having fewer connections than the hubs) of the topological node in addition to the hubs. Further, the MRS can substitute one or more of the hubs with one or more of the nodes. If the resulting variance and other quantitative analysis values are the same or substantially similar to the values determined by using only the hubs, the MRS stores that data, so that in certain situations when a set of physiological data is received by the MRS and the received data is lacking towards a value related to one or more of the hubs, the MRS "knows" that another data value (if available) can be substituted and/or used in place of the missing hub value in making the determination and/or prediction. The MRS can modify learning based on user and/or processing behavior.

Figure 15:
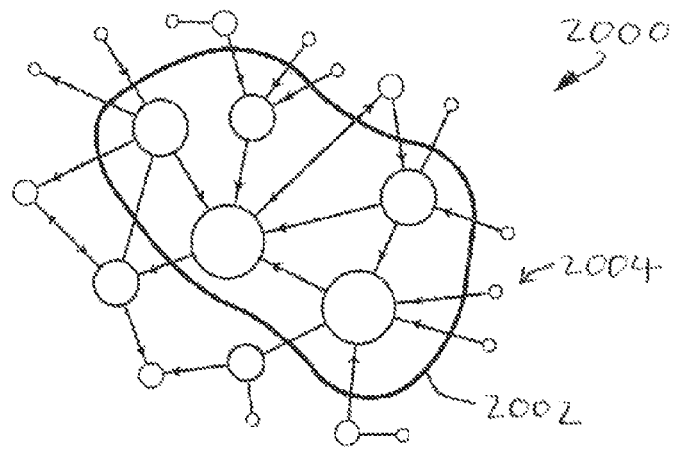
FIGS. 15-17 illustrate another example of an embodiment of the AGI method.
Figure 16:
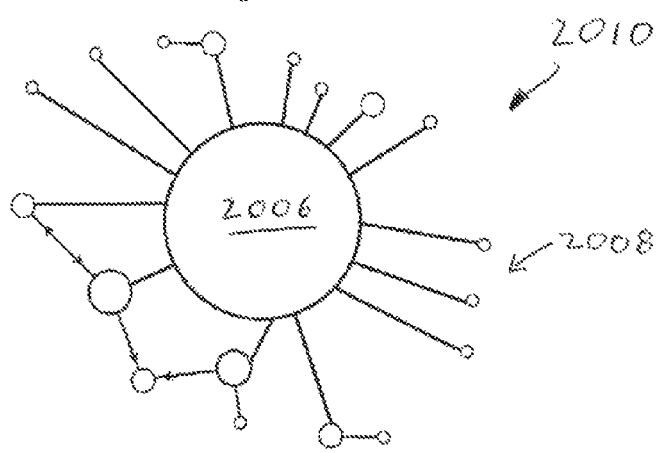
Figure 17:
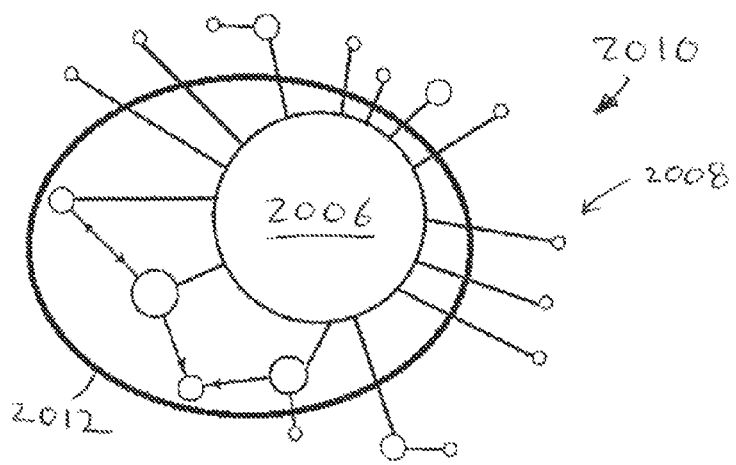

FIGS. 15-17 illustrate an exemplary AGI method which can be performed by the MRS (100 illustrated in FIG. 1) for simplifying a complex network of physiological features to few highly connected hubs for making an inference between two sets of topological modules.

Similar to the visual representation 600 shown in FIG. 6, FIG. 15 illustrates a visual (e.g., schematic) representation 2000 of a topological module 2002 of a disease state (e.g., emergent disease) mapped onto a graph 2004. The MRS can represent one or more clinical descriptors (diseases) as quantifiable association of physiological features and quantifiable data. As illustrated in FIG. 15, clinical descriptors and a disease state can be visually represented as a topological module 2002 having a network of connected nodes (shown as circles that are connected by lines and arrows).

For a very complex disease state, the AGI method performed by the MRS simplifies the complex network of physiological features by grouping various connected nodes that represent a disease state, and collapsing that disease state to a representation of a super node. The super node is treated the same as any other node, but whereas a particular node represents a physiological condition (e.g., a measurable physiological data), the super node represents a quantified data value of a particular disease state determined by the AGI method based on a set of nodes (e.g., hubs inside a topological module). This is AGI method is based on an understanding that some complex disease states are caused by, at least in part, an underlying disease state (or disease states). That is, some disease states cause another disease state. Accordingly, in a vast network of nodes, a topology module for a particular disease state can be inside another disease topology module when they are visually represented according to the AGI method.

The MRS applies the AGI method, and takes the topological module 2002 and performs an inference algorithm (e.g., shown in FIG. 10 and described above) for the highly connected nodes (i.e., hubs) inside the topological module 2002, and arrive at a single quantifiable data value representative of the disease state associated by the topological module 2002.

Then, the MRS converts the topological module 2002 and all of the nodes inside that topological module 2002 into a super node 2006 shown in FIG. 16. FIG. 16 illustrates the super node 2006 as a part of the graph 2008 in the visual representation 2010. This information is then saved onto a non-transitory memory of the MRS.

Then, the MRS applies the AGI method to apply another topological module 2012 shown in FIG. 17 to the network of nodes, which includes the super node 2006 (in place of the numerous nodes that are inside the topology module 2002 shown in FIG. 15). Thus, the topological module 2012, which would have required consideration of many more nodes, can instead consider fewer nodes (including the super node 2006).

Then the AGI method shown in FIG. 10 and described above can be applied to the topological module 2012 shown in FIG. 17.

Figure 18:
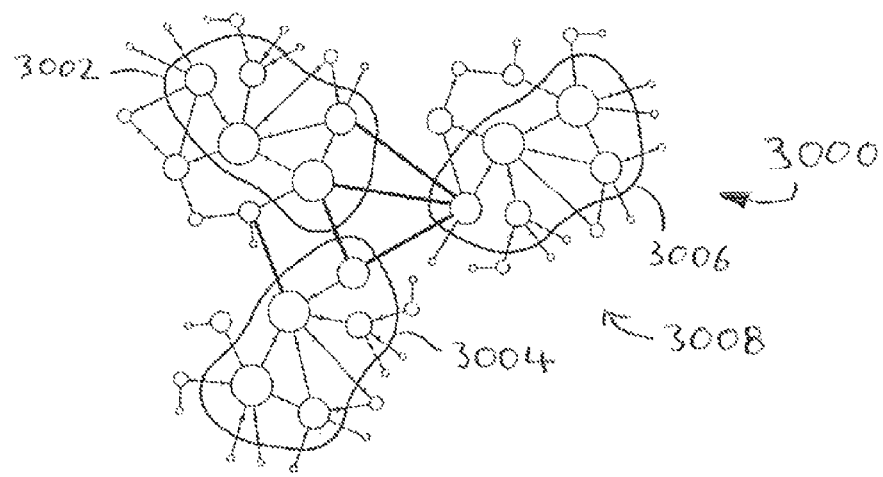
FIGS. 18-20 illustrate yet another example of an embodiment of the AGI method.
Figure 19:
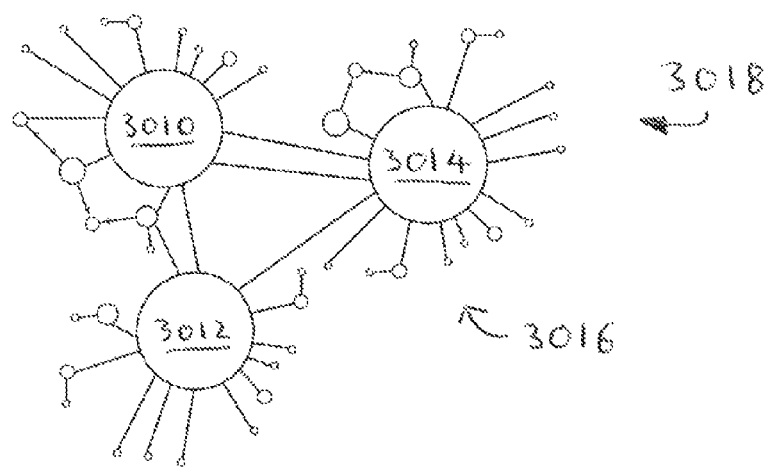
Figure 20:
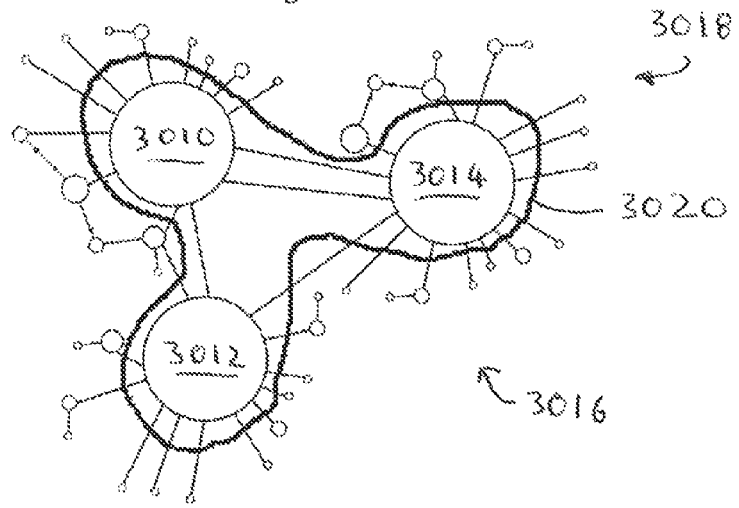

FIGS. 18-20 illustrate another exemplary AGI method which can be performed by the MRS (100 illustrated in FIG. 1) for simplifying an even more complex network of physiological features to few highly connected hubs for making an inference between multiple sets of topological modules.

FIG. 18 illustrates a visual (e.g., schematic) representation 3000 of three topological modules 3002, 3004, 3006 of disease states (e.g., emergent diseases) mapped onto a graph 3008. The three topological modules 3002, 3004, 3006 shown in FIG. 18 do not overlap. However, the three topological modules 3002, 3004, 3006 have nodes that are connected with each other, which indicates some aspects of relation and/or connection between the three disease states represented by the topological modules 3002, 3004, 3006.

The MRS applies the AGI method, as described above in regards to FIGS. 15 and 16, for each of the three topological modules 3002, 3004, 3006. FIG. 19 illustrates the super nodes 3010, 3012, 3014 which has replaced the topological modules 3002, 3004, 3006 and the nodes contained in each of the topological modules 3002, 3004, 3006 (shown in FIG. 18). Accordingly, FIG. 19 illustrates the super nodes 3010, 3012, 3014 as a part of the graph 3016 in the visual representation 3018. This information is then saved onto a non-transitory memory of the MRS.

Based on the graph 3016 in the visual representation 3018, the MRS can determine that the super nodes 3010, 3012, 3014 are highly connected to each other. Further, the MRS can apply another topological module 3020 shown in FIG. 20 onto the graph 3016, which includes the super nodes 3010, 3012, 3014. Thus, the topological module 3020, which would have required consideration of many more nodes, can instead consider fewer nodes (including the super nodes 3010, 3012, 3014).

Then the AGI method shown in FIG. 10 and described above can be applied to the topological module 3020 shown in FIG. 20.

Accordingly, the exemplary methods shown in FIGS. 15-20 can dramatically simplify very complex network of connected nodes, by applying the AGI method to topological modules with the understanding that some disease states are caused by another one or more disease states. It will be understood that a topology module can include one or more topology modules and one or more nodes. Thus, the super node can be considered with other nodes when applying the AGI methodology described herein (e.g., the method shown in FIG. 10 and described above).

With regard to the foregoing description, it is to be understood that changes may be made in detail without departing from the scope of the present invention. It is intended that the specification and depicted embodiment to be considered exemplary only, with a true scope and spirit of the invention being indicated by the broad meaning of the claims.

What is claimed is:

1. A computer-implemented method for determining a disease state of a patient, the method comprising:
   a processor accessing from a computer-readable non-transitory memory, computer-readable data representing a general graph having nodes of physiological conditions, wherein each of the physiological conditions is represented by each of the nodes, wherein each of the nodes is connected by one or more edges representing correlations between the nodes;
   the processor accessing from the computer-readable non-transitory memory, computer-readable data of physiological conditions of a patient;
   the processor executing computer-readable instructions for quantification of the physiological conditions of the patient;
   the processor transforming the physiological conditions of the patient to node data by performing quantification of the physiological conditions of the patient;
   the processor executing computer-readable instructions for associating the node data to the general graph;
   the processor creating an individualized graph by associating the node data to the general graph;
   the processor storing the individualized graph to the computer-readable non-transitory memory;
   the processor accessing from the computer-readable non-transitory memory, computer-readable data representing a topological module of nodes connected by edges, wherein the topological module represents the disease state;
   the processor executing computer-readable instructions for mapping the topological module representing the disease state to the individualized graph;
   the processor executing computer-readable instructions for determining a weight averaged value of the node data of the topological module of nodes;
   the processor determining the disease state of the patient from the weight averaged value;
   the processor executing computer-readable instructions for creating a new general graph by replacing all of the nodes inside the topological module in the general graph with a super node of the weight averaged value; and
   the processor storing the new general graph to the computer-readable non-transitory memory.

2. The computer-implemented method as in claim 1, further comprising:
   the processor accessing from the computer-readable non-transitory memory, additional computer-readable data representing another topological module which includes the super node, wherein the topological module represents another disease state;
   the processor executing computer-readable instructions for mapping the another topological module representing the another disease state to the individualized graph; and
   the processor executing computer-readable instructions for determining another weight averaged value of the super node and other data of the another topological module.

3. The computer-implemented method as in claim 2, further comprising:
   the processor mapping the another topological module to the individualized graph, wherein the another disease state is an emergent disease state.

4. The computer-implemented method as in claim 2, further comprising:
   the processor mapping the another topological module to the individualized graph, wherein the another disease state is a pre-emergent disease state.

5. A computer-implemented method for determining a second disease state of a patient, the method comprising:
   a processor accessing from a computer-readable non-transitory memory, computer-readable data representing a general graph having nodes of physiological conditions and at least one super node representative of a first disease state, wherein each of the physiological conditions is represented by each of the nodes, wherein each of the nodes and the at least one super node is connected by one or more edges representing correlations between the nodes and at least one super node;
   the processor accessing from the computer-readable non-transitory memory, computer-readable data of physiological conditions of a patient;
   the processor executing computer-readable instructions for quantification of the physiological conditions of the patient;
   the processor transforming the physiological conditions of the patient to node data by performing quantification of the physiological conditions of the patient;
   the processor executing computer-readable instructions for associating the node data to the general graph;
   the processor creating an individualized graph by associating the node data to the general graph;
   the processor storing the individualized graph to the computer-readable non-transitory memory;
   the processor accessing from the computer-readable non-transitory memory, computer-readable data representing a topological module of nodes and at least one super node connected by edges, wherein the topological module represents the second disease state;
   the processor executing computer-readable instructions for mapping the topological module representing the second disease state to the individualized graph;
   the processor executing computer-readable instructions for determining a weight averaged value of the node data and the at least one super node of the topological module; and
   the processor determining the second disease state of the patient from the weight averaged value.

6. A medical general intelligence computer, comprising:
   a processor; and
   a computer-readable non-transitory memory in communication with the processor, the computer-readable non-transitory memory including processor-executable instructions for determining a pre-emergent disease state of a patient, wherein when the processor executes the processor-executable instructions, the processor storing on the computer-readable non-transitory memory, computer-readable data representing a general graph of physiological conditions and at least one disease state, wherein each of the physiological conditions is represented as a node of the general graph, and the at least one disease state is represented as a super node of the general graph, wherein each of the nodes and the super node is connected by one or more edges representing correlations between the nodes and the super node;

the processor storing on the computer-readable non-transitory memory, computer-readable data representing a topological module of the nodes and the super node connected by edges, wherein the topological module represents the second disease state, and the topological module can be mapped onto a portion of the general graph; and the processor storing on the computer-readable non-transitory memory, a weight averaged value of nodes and the super node of the portion of the general graph that has been mapped onto by the topological module for determining a second disease state.

* * * * *